(12) United States Patent
Dueck et al.

(10) Patent No.: US 9,440,073 B2
(45) Date of Patent: Sep. 13, 2016

(54) COCHLEAR IMPLANT STIMULATION

(71) Applicant: Cochlear Limited, Macquarie University, NSW (AU)

(72) Inventors: Wolfram Frederik Dueck, Sydney (AU); Nicholas Charles Kendall Pawsey, North Ryde (AU); Peter Raymond Sibary, Luddenham (AU); Claudia Tasche, Bamboka (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 14/799,764

(22) Filed: Jul. 15, 2015

(65) Prior Publication Data

US 2016/0015975 A1    Jan. 21, 2016

Related U.S. Application Data

(60) Provisional application No. 62/026,773, filed on Jul. 21, 2014.

(51) Int. Cl.
*A61N 1/00* (2006.01)
*A61N 1/36* (2006.01)
*A61N 1/05* (2006.01)

(52) U.S. Cl.
CPC ......... *A61N 1/36032* (2013.01); *A61N 1/0541* (2013.01)

(58) Field of Classification Search
CPC ... A61N 1/36032; A61N 1/0541; A61N 1/31
See application file for complete search history.

(56) References Cited

U.S. PATENT DOCUMENTS

| | | | |
|---|---|---|---|
| 4,532,930 A | 8/1985 | Crosby et al. | |
| 7,194,314 B1 * | 3/2007 | Richter | A61N 1/36032 600/25 |
| 8,834,545 B2 * | 9/2014 | Stafford | A61N 5/0622 607/137 |
| 2012/0143284 A1 | 6/2012 | Capcelea et al. | |
| 2012/0158095 A1 | 6/2012 | Jolly | |
| 2012/0191146 A1 | 7/2012 | Markey et al. | |
| 2013/0138194 A1 | 5/2013 | Carter | |

OTHER PUBLICATIONS

Snyder, et al., "Cochlear Implant Electrode Configuration Effects on Activation Threshold and Tonotopic Selectivity," NIH Public Access, Hear Res. Author manuscript; available in PMC Jan. 1, 2009, 25 pages.

(Continued)

*Primary Examiner* — Robert N Wieland
(74) *Attorney, Agent, or Firm* — Edell, Shapiro & Finnan, LLC

(57) ABSTRACT

Presented herein are trans-modiolar stimulation techniques in which stimulation current is sourced (delivered) by at least one intra-cochlear stimulating contact and is sunk at a group of other intra-cochlear stimulating contacts. The group of other intra-cochlear stimulating contacts is positioned (located) across a section of the recipient's modiolus from the intra-cochlear stimulating contact that sources the stimulation. As such, stimulation current generally passes through the modiolus to stimulate spiral ganglion cells and evoke a hearing percept.

18 Claims, 15 Drawing Sheets

(56) References Cited

OTHER PUBLICATIONS

Bierer, et al., "Partial Tripolar Cochlear Implant Stimulation: Spread of Excitation and Forward Masking in the Inferior Colliculus," NIH Public Access, Hear Res. Author manuscript; available in PMC Dec. 1, 2011, 23 pages.

International Search Report and Written Opinion in counterpart International Application No. PCT/IB2015/055357, mailed Nov. 19, 2015, 13 pages.

* cited by examiner

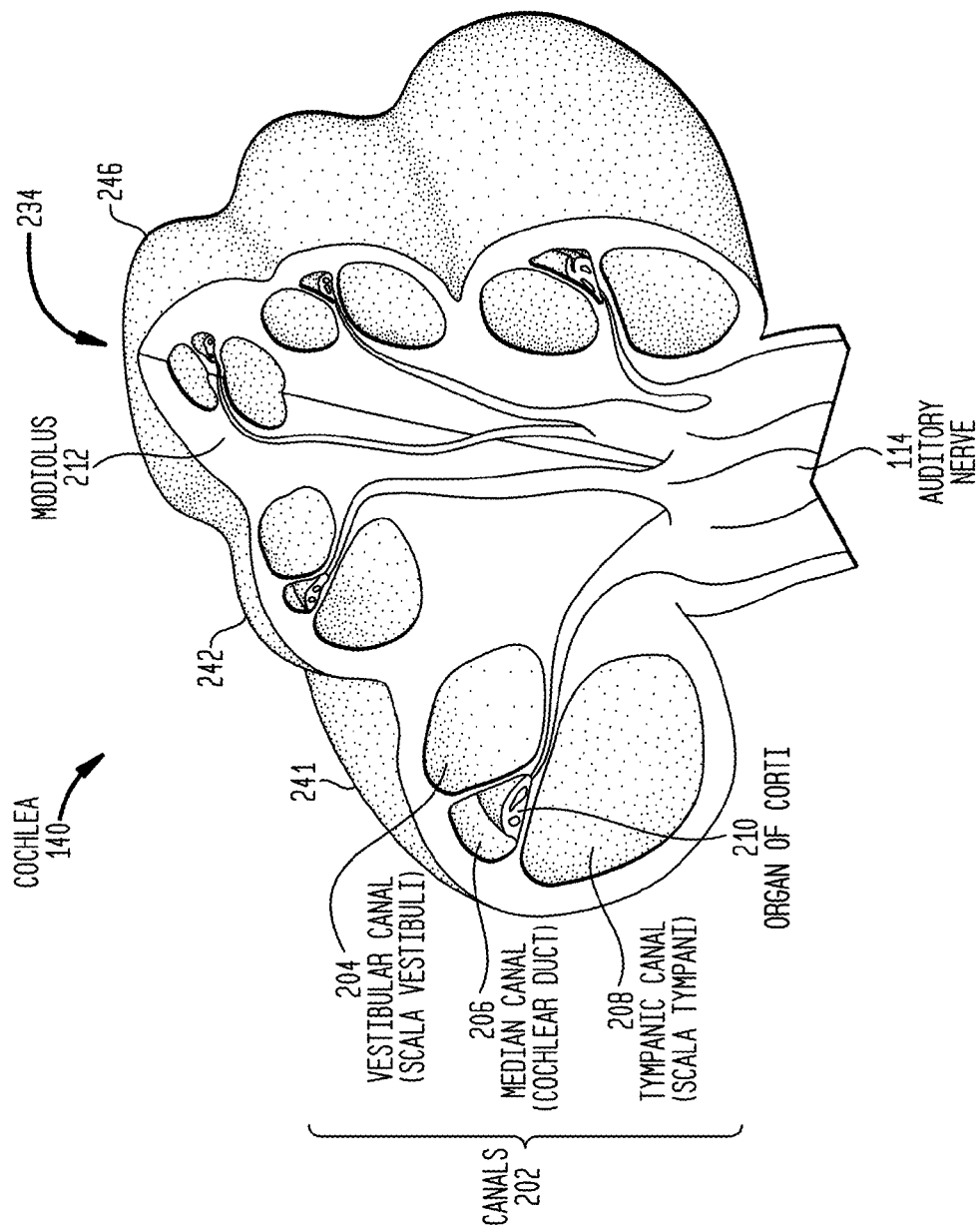

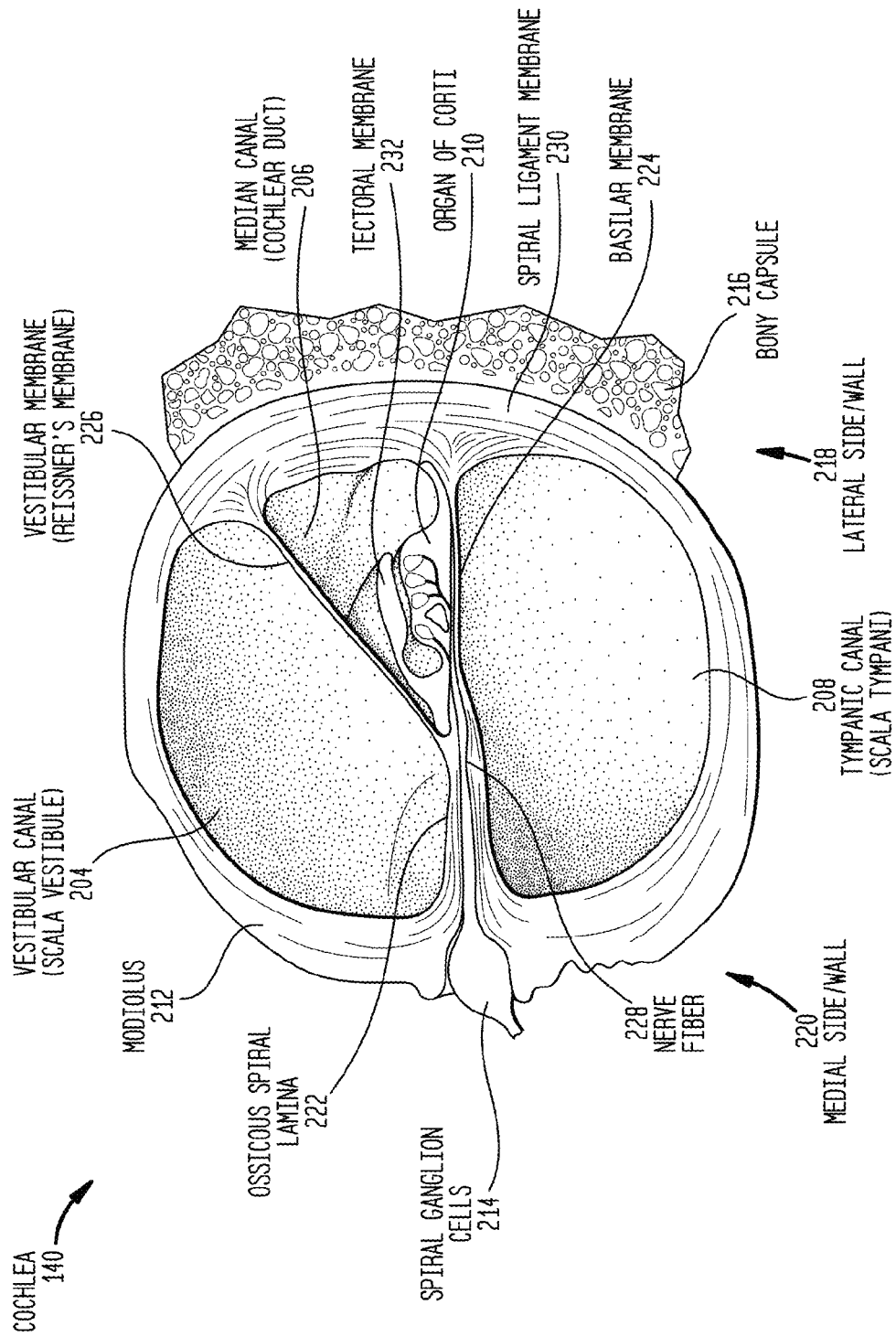

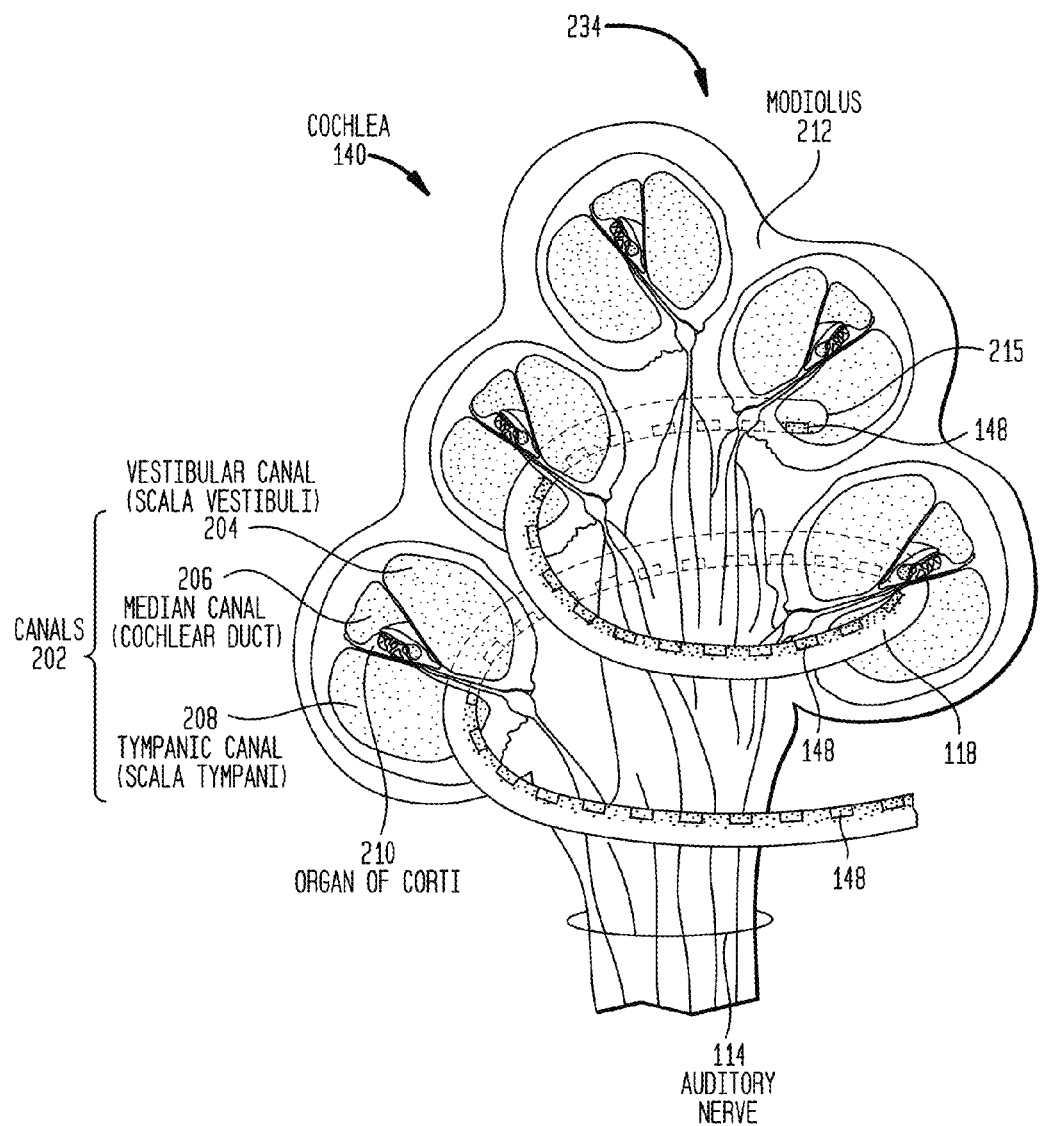

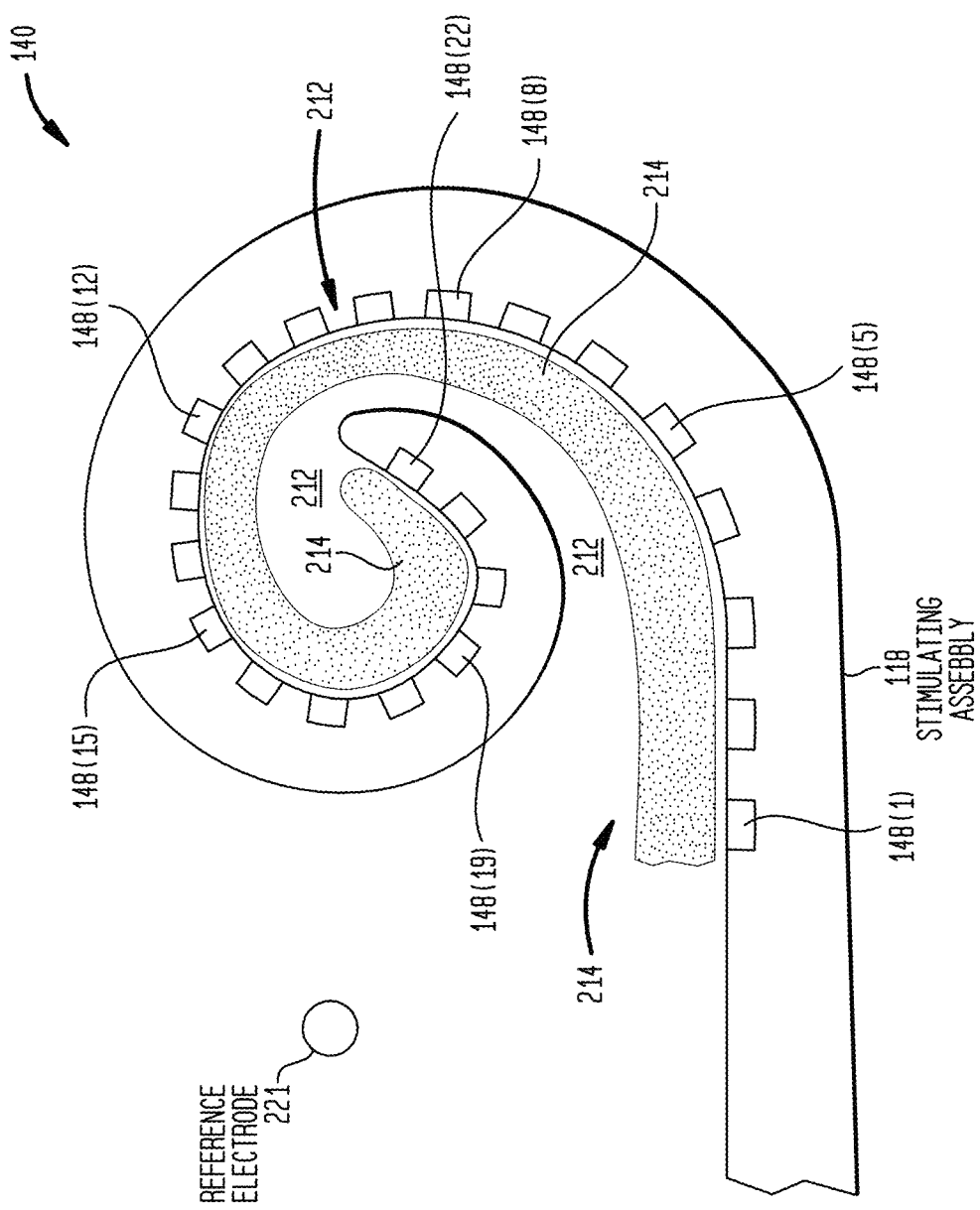

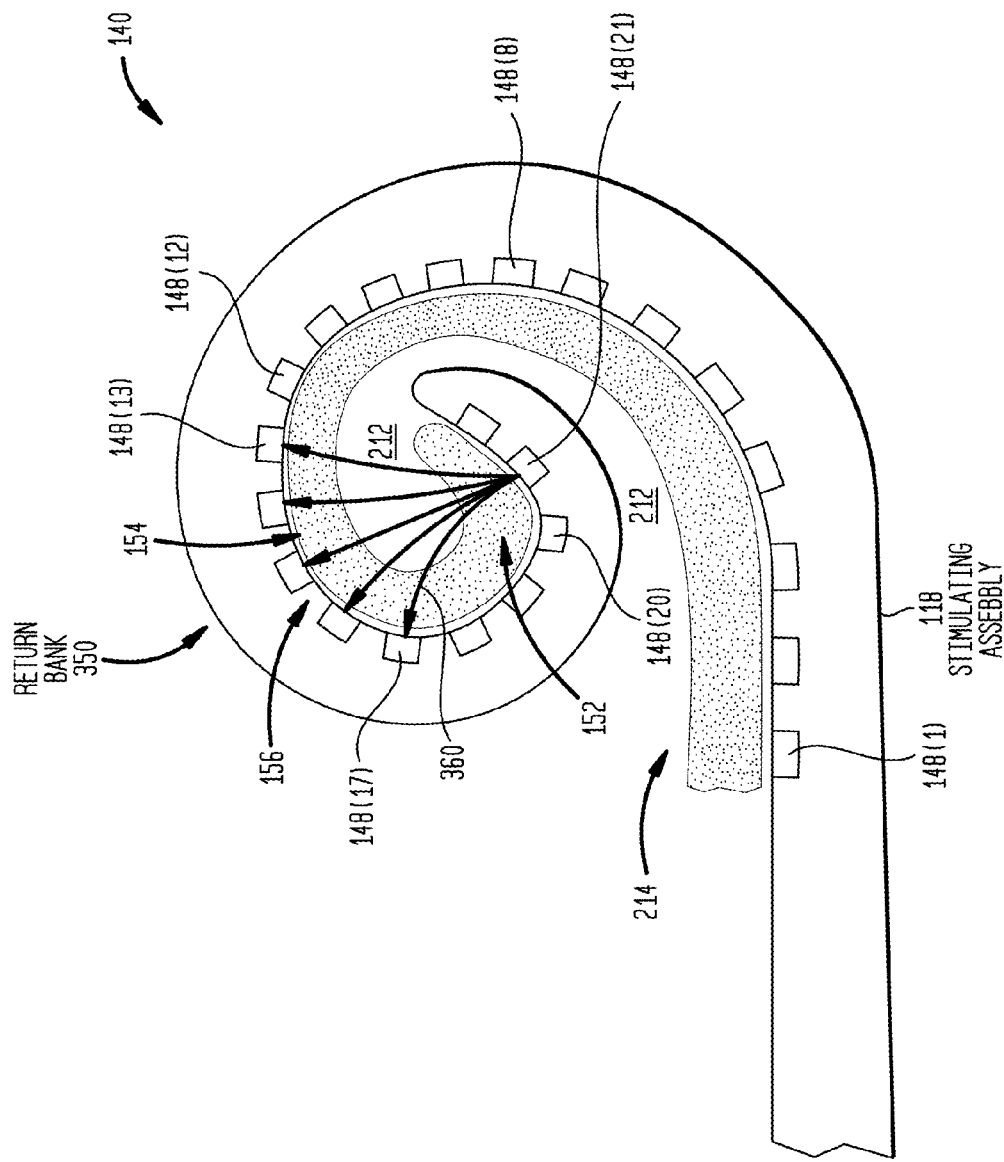

1072 — DELIVERING STIMULATION CURRENT VIA AT LEAST ONE STIMULATING CONTACT SUCH THAT THE STIMULATION CURRENT ENTERS THE MODIOLUS AT A FIRST POPULATION OF SPIRAL GANGLION CELLS

1074 — SINKING THE STIMULATION CURRENT VIA A PLURALITY OF OTHER STIMULATING CONTACTS SUCH THAT THE STIMULATION CURRENT EXITS THE MODIOLUS AT A SECOND POPULATION OF SPIRAL GANGLION CELLS THAT IS PHYSICALLY SEPARATED FROM THE FIRST POPULATION OF SPIRAL GANGLION CELLS

COCHLEAR IMPLANT STIMULATION

CROSS-REFERENCE TO RELATED APPLICATIONS

The present application claims priority to U.S. Provisional Patent Application No. 62/026,773, filed on Jul. 21, 2014, the content of which is hereby incorporated by reference herein.

BACKGROUND

1. Field of the Invention

The present invention relates generally to cochlear implant stimulation.

2. Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

SUMMARY

In one aspect of the invention, a cochlear implant is provided. The cochlear implant comprises a stimulating assembly comprising a plurality of stimulating contacts configured to be implanted in a recipient's cochlea such that the stimulating assembly spirals around at least a portion of the cochlea's modiolus, and a stimulator unit configured to deliver stimulation current to the modiolus via at least one stimulating contact and configured to sink the stimulation current via a plurality of other stimulating contacts such that the stimulation current enters the modiolus at a first population of spiral ganglion cells and exits the modiolus at a second population of spiral ganglion cells that is physically separated from the first population of spiral ganglion cells.

In another aspect of the invention, a cochlear implant is provided. The cochlear implant comprises: a stimulating assembly configured to be implanted in a recipient's cochlea so as to spiral around at least a portion of the cochlea modiolus and comprising a plurality of stimulating contacts, and a plurality of independently operable current sources, wherein a first current source among the plurality of current sources is configured to deliver trans-modiolar stimulation to the cochlea.

In another aspect of the invention, a method for stimulating a recipient of a cochlear implant that includes a plurality of stimulating contacts configured to be implanted in a recipient's cochlea such that the stimulating contacts are disposed around at least a portion of the cochlea modiolus is provided. The method comprises delivering stimulation current via at least one stimulating contact such that the stimulation current enters the modiolus at a first population of spiral ganglion cells, and sinking the stimulation current via a plurality of other stimulating contacts such that the stimulation current exits the modiolus at a second population of spiral ganglion cells that is physically separated from the first population of spiral ganglion cells.

BRIEF DESCRIPTION OF THE DRAWINGS

Embodiments of the present invention are described herein in conjunction with the accompanying drawings, in which:

FIG. 2A is a perspective view of a recipient's cochlea that has been partially cut-away to display the canals and nerve fibers of the cochlea;

FIG. 2B is a cross-sectional view of one turn of the canals of the cochlea of FIG. 2A;

FIG. 2C is a cross-sectional view illustrating the position of a stimulating assembly in the cochlea of FIG. 2A;

FIG. 2D is a schematic further illustrating the position of a stimulating assembly in the cochlea of FIG. 2A;

FIG. 3A is a schematic diagram illustrating the delivery of trans-modiolar stimulation to a recipient's cochlea in accordance with embodiments presented herein;

FIG. 10 is a flowchart of a method in accordance with embodiments presented herein.

DETAILED DESCRIPTION

Presented herein are trans-modiolar stimulation techniques in which stimulation current is sourced (delivered) by at least one intra-cochlear stimulating contact and is sunk at a group of other intra-cochlear stimulating contacts. The group of other intra-cochlear stimulating contacts is positioned (located) across a section of the recipient's modiolus from the intra-cochlear stimulating contact that sources the stimulation. As such, stimulation current generally passes through the modiolus to stimulate spiral ganglion cells and evoke a hearing percept.

Figure 1:
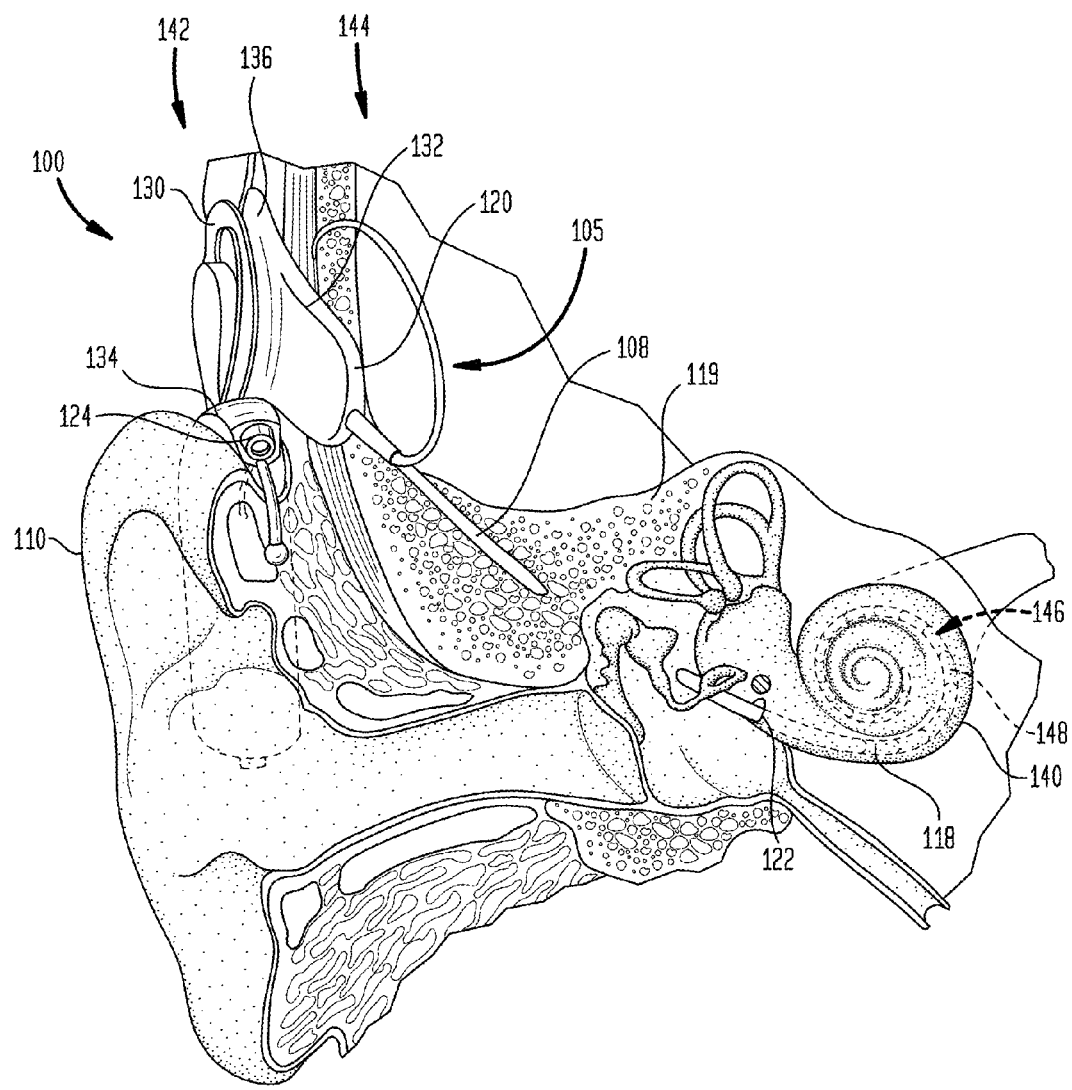
FIG. 1 is a schematic diagram of a cochlear implant configured to deliver trans-modiolar stimulation to a recipient's cochlea in accordance with embodiments presented herein.

FIG. 1 is perspective view of an exemplary cochlear implant 100 configured to execute trans-modiolar stimulation techniques in accordance with embodiments presented herein. The cochlear implant 100 includes an external component 142 and an internal or implantable component 144. The external component 142 is directly or indirectly attached to the body of the recipient and typically comprises an external coil 130 and, generally, a magnet (not shown in FIG. 1) fixed relative to the external coil 130, one or more sound input elements 124 (e.g., microphones, telecoils, etc.) for detecting sound and a sound processing unit 134. The sound processing unit 134 may include, for example, a power source (not shown in FIG. 1) and a sound processor (also not shown in FIG. 1). The sound processor is configured to process electrical signals generated by a sound input element 124 that is positioned, in the depicted embodiment, by auricle 110 of the recipient. The sound processor provides the processed signals to external coil 130 via a cable (not shown in FIG. 1).

FIG. 1 illustrates an example in which cochlear implant 100 includes an external component 142 with an external sound processor. It is to be appreciated that the use of an external component is merely illustrative and that the techniques presented herein may be used in arrangements having an implanted sound processor (e.g., totally implantable cochlear implants). It is also to be appreciated that the individual components referenced herein, e.g., sound input element 124 and the sound processor in sound processing unit 134, may be distributed across more than one tissue-stimulating prosthesis, e.g., two cochlear implants 100, and indeed across more than one type of device, e.g., cochlear implant 100 and a consumer electronic device or a remote control of the cochlear implant 100.

The implantable component 144 comprises an implant body 105, a lead region 108, and an elongate stimulating assembly 118. The implant body 105 comprises a stimulator unit 120, an internal coil 136, and an internal receiver/transceiver unit 132, sometimes referred to herein as transceiver unit 132. The transceiver unit 132 is connected to the internal coil 136 and, generally, a magnet (not shown) fixed relative to the internal coil 136.

The magnets in the external component 142 and implantable component 144 facilitate the operational alignment of the external coil 130 with the internal coil 136. The operational alignment of the coils enables the internal coil 136 to transmit/receive power and data to/from the external coil 130. More specifically, in certain examples, external coil 130 transmits electrical signals (e.g., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding. In use, transceiver unit 132 may be positioned in a recess of the temporal bone of the recipient. Various other types of energy transfer, such as infrared (IR), electromagnetic, capacitive and inductive transfer, may be used to transfer the power and/or data from an external device to cochlear implant and FIG. 1 illustrates only one example arrangement.

Elongate stimulating assembly 118 is at least partially implanted in cochlea 140 and includes a contact array 146 comprising a plurality of intra-cochlear stimulating contacts 148. Contact array 146 may comprise electrical contacts and/or optical contacts. In general, the trans-modiolar techniques are implemented using the electrical contacts that deliver electrical stimulation signals (i.e., current signals) to a recipient.

Stimulating assembly 118 extends through cochleostomy 122 and has a proximal end connected to stimulator unit 120 via lead region 108 that extends through mastoid bone 119. Lead region 108 couples the stimulating assembly 118 to implant body 105 and, more particularly, stimulator unit 120.

In general, the sound processor in sound processing unit 134 is configured to execute sound processing and coding to convert a detected sound into a coded signal corresponding to electrical signals for delivery to the recipient. The coded signal generated by the sound processor is then sent to the stimulator unit 120 via the RF link between the external coil 130 and the internal coil 136. The stimulator unit 120 includes one or more circuits that use the coded signals, received via the transceiver unit 132, so as to output a series of electrical stimulation signals (stimulation current) via one or more stimulation channels that terminate in the intra-cochlear stimulating contacts 148. As such, the stimulation current is delivered to the recipient via the intra-cochlear stimulating contacts 148. In this way, cochlear implant 100 stimulates the recipient's auditory nerve cells, bypassing absent or defective hair cells that normally transduce acoustic vibrations into neural activity. As described further below, the stimulator unit 120 includes a plurality of current sources that can independently source (deliver) and sink electrical current at the intra-cochlear stimulating contacts 148.

Before describing further details of the trans-modiolar stimulation techniques, aspects of cochlea 140 are described first below with reference to FIGS. 2A and 2B. Additionally, the positioning of stimulating assembly 118 within cochlea 140 is shown in greater detail in FIGS. 2C and 2D.

FIG. 2A is a perspective view of cochlea 140 partially cut-away to display the canals and nerve fibers of the cochlea. FIG. 2B is a cross-sectional view of one turn of the canals of cochlea 140. To facilitate understanding, the following description will reference the cochlea illustrated in FIGS. 2A and 2B as cochlea 140, which was introduced above with reference to FIG. 1.

Referring to FIG. 2A, cochlea 140 is a conical spiral structure comprising three parallel fluid-filled canals or ducts, collectively and generally referred to herein as canals 202. Canals 202 comprise the tympanic canal 208, also referred to as the scala tympani 208, the vestibular canal 204, also referred to as the scala vestibuli 204, and the median canal 206, also referred to as the scala media 206. Cochlea 140 spirals about modiolus 212 several times and terminates at cochlea apex 234.

Referring next to FIG. 2B, separating canals 202 of cochlear 140 are various membranes and other tissue. The Ossicous spiral lamina 222 projects from modiolus 212 to separate scala vestibuli 204 from scala tympani 208. Toward lateral side 218 of scala tympani 208, a basilar membrane 224 separates scala tympani 208 from scala media 206. Similarly, toward lateral side 218 of scala vestibuli 204, a vestibular membrane 226, also referred to as the Reissner's membrane 226, separates scala vestibuli 204 from scala media 206.

Portions of cochlea 140 are encased in a bony capsule 216. Bony capsule 216 resides on lateral side 218 (the right side as illustrated in FIG. 2B), of cochlea 140. Spiral ganglion cells 214 reside on the opposing medial side 220 (the left side as illustrated in FIG. 2B) of cochlea 140. A spiral ligament membrane 230 is located between lateral side 218 of spiral tympani 208 and bony capsule 216, and between lateral side 218 of scala media 206 and bony capsule 216. Spiral ligament 230 also typically extends around at least a portion of lateral side 218 of scala vestibuli 204.

The fluid in tympanic and vestibular canals 208, 204, referred to as perilymph, has different properties than that of the fluid which fills scala media 206 and which surrounds organ of Corti 210, referred to as endolymph. Sound entering auricle 110 causes pressure changes in cochlea 140 to travel through the fluid-filled tympanic and vestibular canals 208, 204. As noted, organ of Corti 210 is situated on basilar membrane 224 in scala media 206. It contains rows of 16,000-20,000 hair cells (not shown) which protrude from its surface. Above them is the tectoral membrane 232 which moves in response to pressure variations in the fluid-filled tympanic and vestibular canals 208, 204. Small relative movements of the layers of membrane 232 are sufficient to cause the hair cells in the endolymph to move thereby causing the creation of a voltage pulse or action potential which travels along the associated nerve fiber 228. Nerve fibers 228, embedded within spiral lamina 222, connect the hair cells with the spiral ganglion cells 214 which form auditory nerve 114. Auditory nerve 114 relays the impulses to the auditory areas of the brain (not shown) for processing.

The place along basilar membrane 224 where maximum excitation of the hair cells occurs determines the perception of pitch and loudness according to the place theory. Due to this anatomical arrangement, cochlea 140 has characteristically been referred to as being "tonotopically mapped." That is, regions of cochlea 140 toward basal region 116 are responsive to high frequency signals, while regions of cochlea 140 toward apical end 116 are responsive to low frequency signals. These tonotopical properties of cochlea 140 are exploited in a cochlear implant by delivering stimulation signals within a predetermined frequency range to a region of the cochlea that is most sensitive to that particular frequency range.

FIG. 2C is a cross-sectional view of cochlea 140 in which stimulating assembly 118 has been implanted therein, while FIG. 2B is a simplified top view of the cochlea 140 in which stimulating assembly 118 has been implanted therein. The stimulating assembly 118 is typically inserted through an opening (e.g., the round window or a cochleostomy) in the basal end of the recipient's scala tympani 208. When implanted, the stimulating assembly 118 follows the helical shape of the cochlea 140. That is, the stimulating assembly 118, and thus the stimulating contacts 148 disposed therein, spirals around the modiolus 212.

There are a variety of types of intra-cochlear stimulating assemblies that may be inserted into a recipient's cochlea. For example, a perimodiolar stimulating assembly is a stimulating assembly that is configured to adopt a curved configuration during and/or after implantation into the recipient's cochlea. To achieve this, the stimulating assembly may be pre-curved to the same general curvature of a cochlea. Perimodiolar stimulating assemblies are typically held straight by, for example, a stiffening stylet or sheath which is removed during implantation. Varying material combinations or shape memory materials may also be used so that the stimulating assembly may adopt its curved configuration when in the cochlea. A stimulating assembly can also be a non-perimodiolar stimulating assembly. A non-perimodiolar stimulating assembly may be a substantially straight assembly, a mid-scala assembly which assumes a midscale position during or following implantation, or a short assembly electrode implanted into at least a basal region of the cochlea. The stimulating assembly may extend towards apical end of cochlea, referred to as the cochlea apex 234.

As shown in FIGS. 2C and 2D, the stimulating assembly 118 is configured to assume a modiolar position (i.e., a position close to the modiolus 212) during or after insertion. In this position, the intra-cochlear stimulating contacts 148 are adjacent to the spiral ganglion cells 214 of the modiolus 212. In the specific embodiments illustrated herein, stimulating assembly 118 comprises twenty-two (22) intra-cochlear stimulating contacts 148(1) through 148(22). Intra-cochlear stimulating contact 148(1) is the most basal stimulating contact (i.e., located closest to the basal end of the cochlea 140), while intra-cochlear stimulating contact 148(22) is the most apical stimulating contact (i.e., located closed to the cochlea apex 234). A reference contact 221 may also be provided and electrically connected to the stimulator/receiver unit. Since it is positioned outside of the recipient's cochlea 140, the reference contact 221 is sometimes referred to as an extra-cochlear electrode (ECE).

As noted above, cochlear implants execute sound coding in order to map received sounds into a series of electrical current pulses/signals to be delivered via stimulation channels terminating in electrical stimulating contacts implanted in the cochlea. An important aspect of sound coding is how to preserve the intelligibility and quality of target sounds both in quiet and adverse (e.g., noisy) listening environments. As such, different sound coding algorithms have been developed to mimic the firing patterns inside the cochlea as closely as possible.

A sound coding algorithm may determine, for example, the amplitude, the width, the shape, the timing, and the stimulation channel (place/contact) of a current signal. To mimic the tonotopic organization of the cochlea, sound coding algorithms typically decompose the input sound signal into different frequency bands using a filter bank. The algorithm then extracts envelope amplitude information, sometimes referred to herein as a channel magnitude, in each frequency band. These channel magnitudes are then used to determine the level of stimulation current delivered via a corresponding stimulation channel. Thus, the filter bank emulates the behavior of the cochlea in a normal ear, where different locations along the length of cochlea are sensitive to different frequencies. The number of channel magnitudes (envelopes) and stimulation channels selected for use in stimulating the recipient at each cycle differs for different strategies.

Conventionally, different stimulation methods/modes may be used to deliver electrical stimulation signals to the recipient's cochlea in accordance with a sound coding algorithm (e.g., monopolar stimulation, bipolar stimulation, tripolar stimulation, etc.). Due, at least in part, to the fact that the cochlea is tonotopically mapped (i.e., partitioned into regions that are each responsive to stimulus signals in a particular frequency range) each stimulating contact 148 of the stimulating assembly 118 delivers a stimulation signal to a particular region of the cochlea. That is, in general, stimulation signals delivered via different stimulation channels are intended to stimulate independent populations of spiral ganglion cells 214 within the cochlea 140. In practice, however, when stimulation signals are delivered via a stimulating contact, the stimulation may spread from the contact so as to excite spiral ganglion cells 214 that are not only near the stimulating contact, but also at various distances from the electrical contact. Different stimulation methods result in different levels of current spread, specificity of stimulation and perception thresholds. The trans-modiolar stimulation techniques described herein may increase the localization (focus) of intra-cochlear electrical stimulation while maintaining acceptable efficiency of stimulation.

More specifically, in accordance with the trans-modiolar stimulation techniques, electrical stimulation signals (stimulation current) is sourced (delivered) via at least one infra-cochlear stimulating contact. The at least one intra-cochlear stimulating contact that delivers the stimulation current is referred to herein as a "target stimulating contact" or a "source stimulating contact." A group (plurality) of other intracochlear stimulating contacts positioned (located) across a section of the recipient's modiolus from the target/source stimulating contact sink (draw) at least a portion of sourced stimulation current. In general, the trans-modiolar stimulation current passes through the modiolus to stimulate spiral ganglion cells and evoke a hearing percept. The plurality of other stimulating contacts that sink the stimulation current are sometimes referred to herein individually as "return stimulating contacts" and are sometimes referred to herein collectively as a "return bank."

It is to be appreciated that, due to the symmetrical biphasic nature of the stimulation waveform, stimulating contacts may alternate between sourcing and sinking current (i.e., a stimulating contact may source current during a first part of current delivery, while the same contact may sink during a second part of the current delivery). As such, reference to the "source" and "sink" stimulating contacts are used merely for ease of illustration and is not intended to limit the functionality of the contacts. A defining characteristic of a target stimulating contact is that it is the contact adjacent to the target spiral ganglion population (i.e., the cells that to be stimulated to evoke a hearing percept).

Figure 3B:
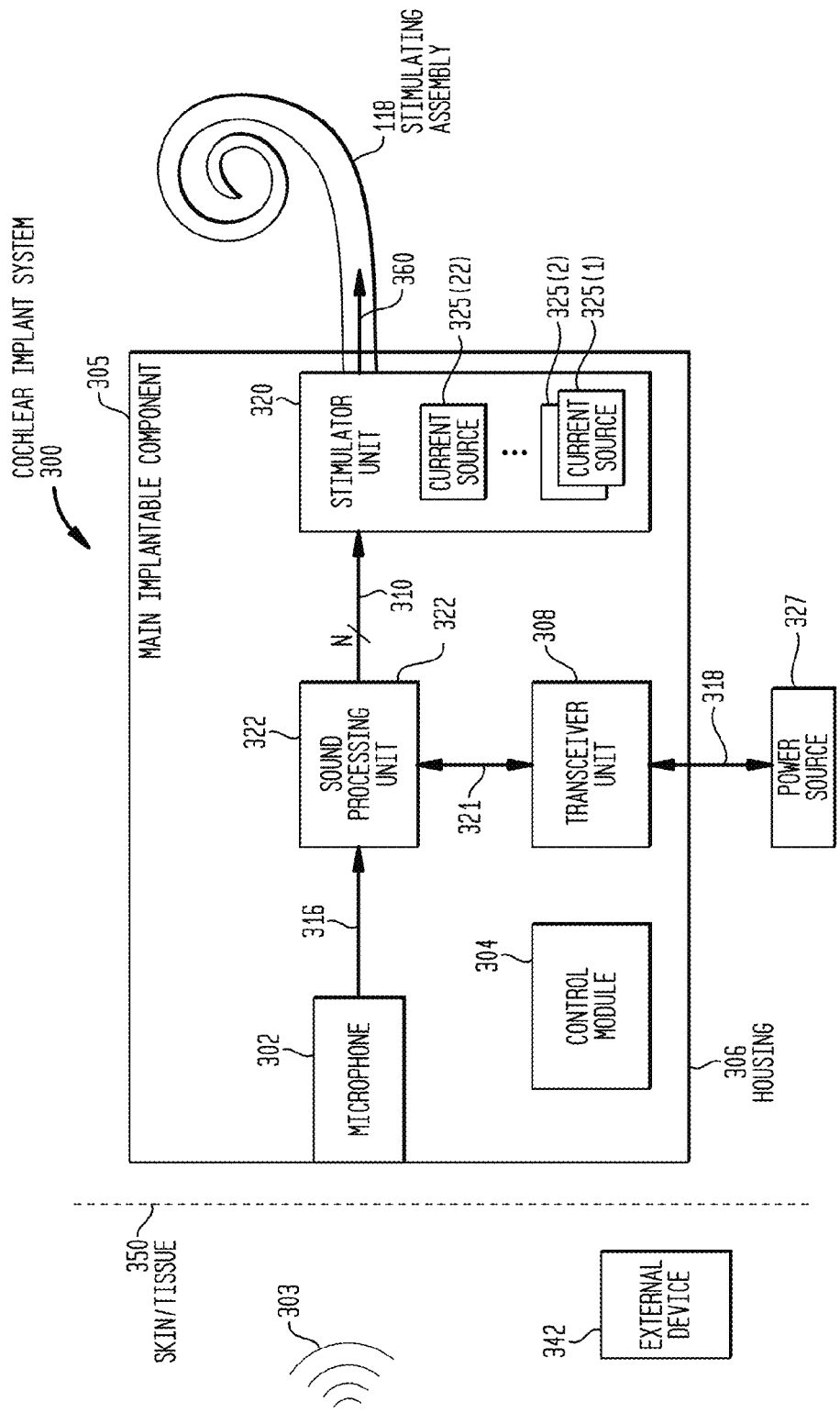
FIG. 3B is a block diagram of a cochlear implant system configured to deliver trans-modiolar stimulation to a recipient's cochlea in accordance with embodiments presented herein.

FIGS. 3A and 3B illustrate further details of current delivery and sinking in accordance with the trans-modiolar stimulating techniques. For ease of illustration, the examples of FIGS. 3A-3B are described with reference to stimulating assembly 118 positioned in cochlea 140 as described above with reference to FIGS. 2C and 2D. It is to be appreciated that this specific arrangement is merely illustrative and other arrangements are possible (i.e., different stimulating assemblies, different intra-cochlear positions, etc.)

Referring first to FIG. 3A, trans-modiolar stimulation current is sourced at stimulating contact 148(21) and the stimulation current is sunk at stimulating contacts 148(13)-148(17). That is, stimulating contact 148(21) is the target/source contact that is adjacent to the target population of cells while stimulating contacts 148(13)-148(17) collectively are return contacts that form a return bank 350. The stimulation current is illustrated in FIG. 3A by arrows 360 and is referred to herein as stimulation current 360. It is to be appreciated that arrows used herein to represent current, such as arrows 360, do not necessarily represent the current field generated within the cochlea, but rather represent the general direction of current flow (i.e., from target contact 148(21) to return contacts 148(13) through 148(17)).

In the embodiment of FIG. 3A, a current source in a stimulator unit delivers current signals (stimulation current 360) to the target contact 148(21). Substantially simultaneously, one or more current sources connected to each of the stimulating contacts 148(13)-148(17) in return bank 350 will sink the stimulation current 360. In this way, the stimulation current 360 is pulled/directed from the target contact 148(21) through the return contacts 148(13)-148(17) and thus to the sinking current sources. In this manner, a substantial portion of the stimulation current 360 passes completely through the modiolus 212 (i.e., passes from one side of the modiolus to another side of the modiolus). That is, a large percentage of the current enters the modiolus 212 at a first location and exits the modiolus 212 at a different location that is non-adjacent to the first location. The amount or percentage of current that will pass from the stimulating contacts to the return contacts may depend, in part, on the position of the contacts within the cochlea, particularly the position of the target contact with respect to the modiolar wall. If the target contact is placed close to the modiolar wall (e.g., in intimate contact with the modiolar wall), the bulk of the current should pass through the modiolus instead of through the perilymph.

In FIG. 3A, the stimulation current 360 enters the modiolus 212 at a first discrete population 152 of spiral ganglion cells 214 that is adjacent to target contact 148(21). The first population 152 of the spiral ganglion cells 214 is sometimes referred to herein as the "target" population as this is the region of the cochlea 140 that is intended to be stimulated by the stimulation current 360 so as to evoke a hearing percept of the frequency associated with the target population. The stimulation current 360 exits the modiolus 212 at a second population 154 of spiral ganglion cells 214 that is adjacent to the return contacts 148(13)-148(17). As shown, the second population 154 of spiral ganglion cells 214 is physically separated from the first population 152 of spiral ganglion cells 214. As used herein, a "population" of spiral ganglion cells 214 refers to a group of neurons located generally adjacent to one or more stimulating contacts.

As shown, the return bank 350 has a central point 156 that is centered at a location that is different from the location of the target contact 148(21). In certain embodiments, the central point 156 of the return bank 350 is generally diametrically opposite the location of target contact 148(21) (i.e., the central point 156 is located at an opposing side of the modiolus 212 from the stimulating contact 148(21)).

As noted above, the stimulation current 360 enters the modiolus 212 at the first population 152 of spiral ganglion cells 214 adjacent to target contact 148(21) and exits the modiolus 212 at a second population 154 of spiral ganglion cells 214 adjacent to the return contacts 148(13)-148(17). Due to the tonotopic nature of the cochlea 140, the second population 154 of the spiral ganglion cells 214 adjacent to the return contacts 148(13)-148(17) is responsive to sound frequencies that are different from that of the target population 152. As such, the return bank 350 has a sufficient size/area such that the current density of the stimulation current 360 as it exits the modiolus 212 (and impinges upon the second population 154) is below a firing threshold of the spiral ganglion cells 214 in the second population. That is, the return bank 350 has a sufficient size/area such that level of the stimulation current 360 is reduced, via current spreading induced by the return contacts, to a level that does not evoke a hearing percept of the frequencies associated with the second population 154 of spiral ganglion cells 214. If the level of the stimulation current 360 is too high upon its exit from modiolus 212 firing of the spiral ganglion cells 214 in the second population 154 may occur. If the spiral ganglion cells 214 in the second population 154 fire, the recipient would perceive other frequencies in addition to the target frequency, thereby leading to pitch confusion and reduced sound perception.

The current spreading and the direction of the flow of stimulation current 360 may be affected by the location and/or number of return contacts 148(13)-148(17) in return bank 350. In certain embodiments, the current spreading and the direction of the flow of stimulation current 360 may be further controlled/affected by weighting the amount of current that is sunk at each of the return contacts 148(13)-148(17) in the return bank 350. That is, the current sources that sink current via the return contacts 148(13)-148(17) are independently controllable so as to sink different amounts of current from each of the return contacts (i.e., the current sources and associated circuits/electronics allow the adjustment and programming of how much current is sourced or sunk through each stimulating contact). Table 1, below, illustrates example percentages of the amount of current that is sunk at each of the return contacts 148(13)-148(17) in one illustrative embodiment. In this embodiment, 100% of the current is sourced at target contact 148(21).

TABLE 1

| Return Contact 148(13) | Return Contact 148(14) | Return Contact 148(15) | Return Contact 148(16) | Return Contact 148(16) |
|---|---|---|---|---|
| 22.5% | 20% | 15% | 20% | 22.5% |

In the illustrative example of Table 1, the central stimulating contact 148(15) of the return bank 350 has the lowest weighting and higher weightings are used for the flanking return contacts. This particular weighting assists in maintaining the current density distribution more uniform across the return bank and below the threshold at the second population 154 of spiral ganglion cells 214.

It is to be appreciated that the example weightings of Table 1 are merely illustrative and that the current sink weighting (i.e., the amount of current sunk at each return contact) may depend on a number of different predetermined, measurable, or estimated parameters. For example, due to the anatomy of the cochlea, the weighting may depend on the insertion depth of the source and/or return contacts within the cochlea. In addition or alternatively, weighting may depend on other anatomical properties of the cochlea or on recipient-specific parameters (e.g., the recipient's stimulation parameters such as threshold levels or comfort levels, tonal deafness, neural survival, etc.). Other factors such as the position of the contacts within the scala tympani (e.g., peri-modiolar position, lateral wall position, etc.) may also influence the selected weightings.

FIG. 3A illustrates a return bank 350 that includes five (5) return contacts 148(13)-148(17). It is to be appreciated that the use of five return contacts is merely illustrative that any number of two or more contacts may be used in alternative embodiments. In certain embodiments, the number of return contacts may be selected based, in part, on the relative positions of the source and return contacts in the cochlea. For example, the position of the target contact in the cochlea 140 may affect how much the stimulation current spreads therefrom and/or how much stimulation current enters the nerve. These parameters may be determined/measured and factored in when select the number and location of the return contacts.

Additionally, neural survival may affect stimulation current spread and thus the number and/or location of the return contacts. For example, the target population 152 of the spiral ganglion cells 214 may have a low survival rate such that the population is only responsive to (i.e., will only fire in response to) relatively high levels of stimulation current. The need to deliver a relatively high level of stimulation current to evoke a hearing percept at the target population 152 may correspondingly result in the need for a larger return bank so as to sufficiently spread the stimulation current and thereby avoid percepts at the second population 154. Recipient specific-parameters other than neural survival, such as, the development of fibrous tissue around the stimulating assembly and/or new bone growth within the cochlea may also affect the optimum weightings. This may change over time after implantation as the tissue/bone grows.

The stimulating assembly 118 is electrically connected to an implantable module that delivers stimulation signals to the stimulating contacts 148. FIG. 3B is a functional block diagram illustrating an exemplary implantable module 305 that may be used with the stimulating assembly 118 to form a totally implantable cochlear implant system 300 (i.e., a cochlear implant in which all components are configured to be implanted under skin/tissue 350 of a recipient). Because all components of cochlear implant system 300 are implantable, cochlear implant system 300 operates, for at least a finite period of time, without the need of an external device.

Cochlear implant system 300 includes a main implantable component or implant body 305 having a hermetically sealed, biocompatible housing 306. Disposed in main implantable component 305 is a microphone 302 configured to sense a sound signal 303. Microphone 302 may include one or more components to pre-process the microphone output. As an alternative, the microphone and other aspects of the system can be included in an upgrade or tethered module as opposed to in a unitary body as shown in FIG. 3B.

An electrical signal 316 representing sound signal 303 detected by microphone 302 is provided from the microphone 302 to sound processing unit 322. The sound processing unit 322 implements one or more speech processing and/or coding strategies to convert the pre-processed microphone output into data signals 310 for use by stimulator unit 320. Stimulator unit 320 utilizes data signals 310 to generate stimulation current 360 for delivery to the cochlea 140 of the recipient via stimulating assembly 118.

More specifically and with reference to the specific embodiment of FIG. 3B, the stimulator unit 320 includes a plurality of independently operable current sources 325(1)-325(22). In accordance with the trans-modiolar stimulating techniques, at least one of the current sources, such as current source 325(21), uses the data signals 310 to deliver stimulation current 360 to target contact 148(21) (FIG. 3A). Substantially simultaneously, one or more other current sources, such as current sources 325(13) through 325(17), sink the stimulation current 360 via return contacts 148(13)-148(17).

FIG. 3B illustrates an embodiment in which the main implantable component 305 includes twenty-two (22) current sources, one for each of the twenty-two stimulating contacts 148(1)-148(22). That is, in the embodiment of FIG. 3B there is a one-to-one correspondence between current sources and stimulating contacts. It is to be appreciated that this arrangement is merely illustrative and that a one-to-one correspondence of current sources to stimulating contacts is not necessary. For example, in other embodiments a reduced number of current sources may be selectively connectable to different stimulating contacts (e.g., eleven current sources each selectively connectable to multiple stimulating contacts).

Cochlear implant system 300 also includes a rechargeable power source 327. Power source 327 may comprise, for example, one or more rechargeable batteries. Power may be received from an external device, such as external device 342, and is stored in power source 327. The power may then be distributed to the other components of cochlear implant system 300 as needed for operation. For ease of illustration, main implantable component 305 and power source 327 are shown separate. However, power source 327 can alternatively be integrated into a hermetically sealed housing 306 or part of a separate module coupled to component 305.

Main implantable component 305 further comprises a control module 304. Control 304 includes various components for controlling the operation of cochlear implant system 300, or for controlling specific components of cochlear implant system 300. For example, controller 304 may control the delivery of power from power source 327 to other components of cochlear implant system 300.

As noted above, cochlear implant system 300 further comprises a receiver or transceiver unit that permits cochlear implant system 300 to receive and/or transmit signals to an external device 342. As used herein, transceiver unit 308 refers to any collection of one or more implanted components which form part of a transcutaneous energy transfer system. Furthermore, transceiver unit 308 includes any number of component(s) which receive and/or transmit data or power, such as, for example a coil for a magnetic inductive arrangement, an antenna for an alternative RF system, capacitive plates, or any other suitable arrangement. Various types of energy transfer, such as infrared (IR), electromagnetic, capacitive and inductive transfer, can be used to transfer the power and/or data from external device 342 to cochlear implant system 300.

For ease of illustration, cochlear implant system 300 is shown having a transceiver unit 308 in main implantable component 305. In alternative arrangements, cochlear implant system 300 includes a receiver or transceiver unit which is implanted elsewhere in the recipient outside of main implantable component 305.

As noted, transceiver unit 308 receives power and/or data from external device 342. In the illustrative arrangement of FIG. 3B, external device 342 comprises a power source (not shown) disposed in a behind-the-ear unit. External device 342 also includes components of a transcutaneous energy transfer link formed with transceiver unit 308 to transfer the power and/or data to cochlear implant system 300. The external device shown in FIG. 3B is merely illustrative, and other external devices can be alternatively used.

FIGS. 4-9 illustrate the use of trans-modiolar stimulation techniques in accordance with further embodiments presented herein. For ease of illustration, the examples of FIGS. 4-9 are described with reference to stimulating assembly 118 positioned in cochlea 140 as shown in FIGS. 2C and 2D.

Figure 4:
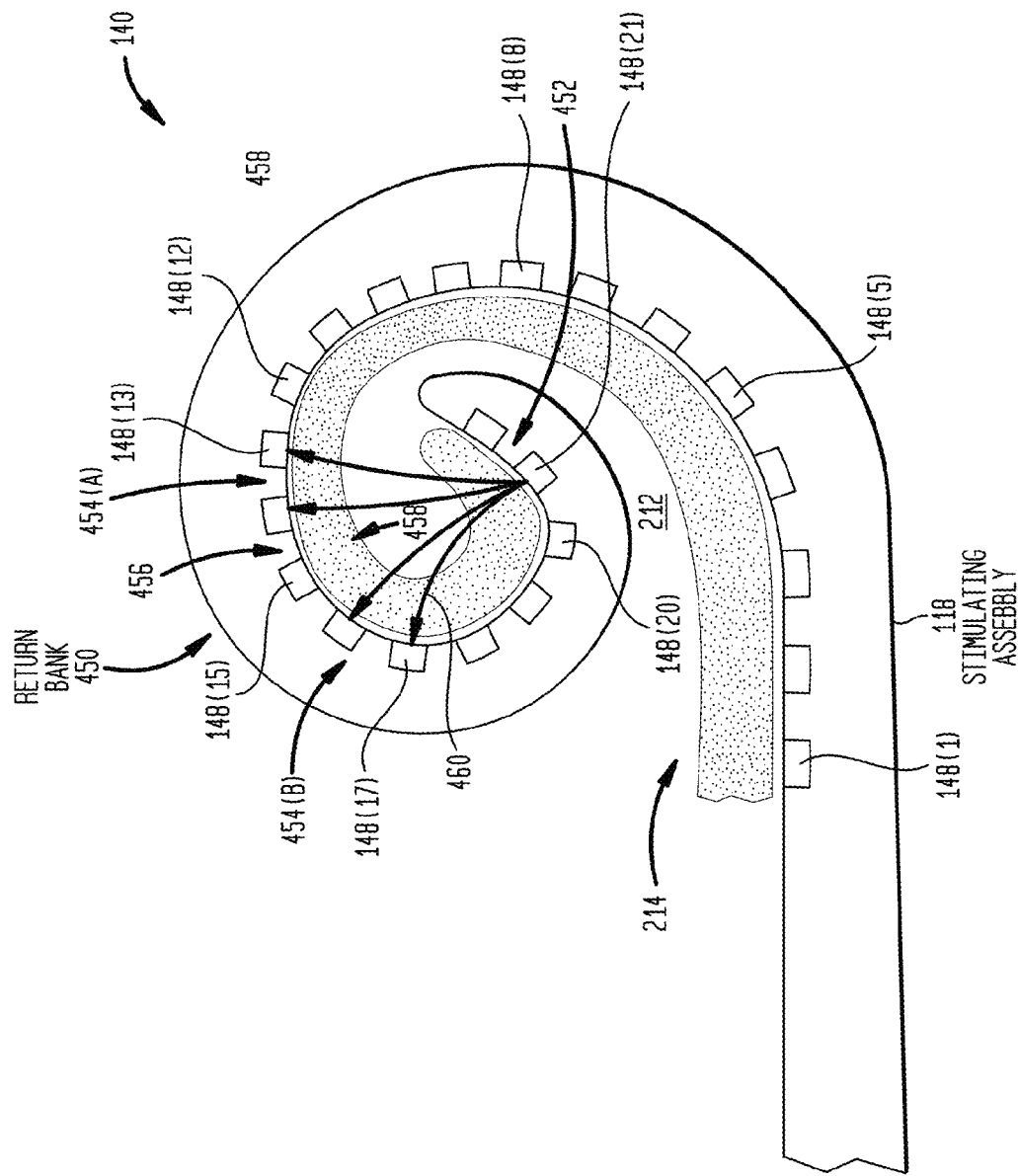
FIG. 4 is a schematic diagram illustrating the delivery of trans-modiolar stimulation to a recipient's cochlea in accordance with embodiments presented herein.

FIG. 4 illustrates an embodiment in which stimulation current is delivered/sourced via stimulating contact 148(21). In this example, the stimulation current is sunk at a return bank 450 that includes non-adjacent return contacts (i.e., return contacts have one or more contacts that do not sink current there between). More specifically, in this example the return bank 450 includes stimulating contacts 148(13), 148(14), 148(16), and 148(17), but does not include stimulating contact 148(15). In other words, the return bank 450 omits stimulating contact 148(15) such that the at least some of the return contacts, namely return contacts 148(14) and 148(16), and 148(17), are no longer a sequence of adjacent contacts. The stimulation current in FIG. 4 is illustrated by arrows 460 and is referred to herein as stimulation current 460.

In the embodiment of FIG. 4, a current source delivers current signals (stimulation current 460) to the target contact 148(21). Substantially simultaneously, one or more current sources connected to each of the stimulating contacts 148(13), 148(14), 148(16), and 148(17) in return bank 450 will sink the stimulation current 460. In this way, the stimulation current 460 is pulled/directed from the target contact 148(21) through the return contacts 148(13), 148(14), 148(16), and 148(17) and thus to the sinking current sources. In this manner, a substantial portion of the stimulation current 460 passes through the modiolus 212.

More specifically, in FIG. 4 the stimulation current 460 enters the modiolus 212 at a first discrete population 452 of spiral ganglion cells 214 that is adjacent to target contact 148(21). The first population 452 of the spiral ganglion cells 214 is sometimes referred to herein as the target population as this is the region of the cochlea 140 that is intended to be stimulated by the stimulation current 460. A first portion of the stimulation current 460 exits the modiolus 212 at a second population 454(A) of spiral ganglion cells 214 that is adjacent to the return contacts 148(13) and 148(14), while a second portion of the stimulation current 460 exits the modiolus 212 at a third population 454(B) of spiral ganglion cells 214 that is adjacent to the return contacts 148(16) and 148(17). As shown, the second and third populations of spiral ganglion cells 214 are each physically separated from the first population 452 of spiral ganglion cells 214.

As shown, the return bank 450 has a central point 456 that is centered at a location that is different from the location of the target contact 148(21). In certain embodiments, the central point 456 of the return bank 450 is generally diametrically opposite the target contact 148(21) (i.e., the central point 456 is located at an opposing side of the modiolus 212 from the stimulating contact 148(21)).

Due to the tonotopic nature of the cochlea 140, the second and third populations 454(A) and 454(B) of the spiral ganglion cells 214 adjacent to the return contacts are responsive to sound frequencies that are different from that of the first (target) population 452. As such, the return bank 450 has a sufficient size/area such that the level of the stimulation current 460 as it exits the modiolus 212 (and impinges upon the second and third populations 454(A) and 454(B)) is below a firing threshold of the spiral ganglion cells 214 in the second population. That is, the level of the stimulation current 460 should be reduced, via current spreading induced by the return contacts, to a level that does not evoke a hearing percept of the frequencies associated with the second and third populations 454(A) and 454(B) of spiral ganglion cells 214.

The current spreading and the direction of the flow of stimulation current 460 may be affected by the location and/or number of return contacts 148(13), 148(14), 148(16), and 148(17) in return bank 450. In certain embodiments, the current spreading and the direction of the flow of stimulation current 460 may be further controlled/affected by weighting the amount of current that is sunk at each of the return contacts 148(13), 148(14), 148(16), and 148(17) in the return bank 650. That is, the current sources that sink current via the return contacts 148(13), 148(14), 148(16), and 148

(17) are independently controllable so as to sink different amounts of current from each of the return contacts.

As noted above, in the embodiment of FIG. 4 stimulating contact 148(15) is omitted from the return bank 450 such that stimulation current 460 is steered or directed away from a population 458 of spiral ganglion cells 214 adjacent to the stimulating contact 148(15). There may be a number of reasons to deliberately steer stimulation current away from a particular stimulating contact or particular spiral ganglion cell population or, conversely, steer current to a particular stimulating contact or particular spiral ganglion cell population. A contact/population may be omitted due to attributes of determined or measured current spread functions, anatomical properties of the cochlea, and/or recipient-specific parameters (e.g., the recipient's stimulation parameters such as threshold levels or comfort levels, tonal deafness, neural survival, etc.)

For example, in one specific embodiment the population 458 of spiral ganglion cells 214 adjacent to the stimulating contact 148(15) may have significant neural survival, while the second and third populations 454(A) and 454(B) of spiral ganglion cells 214 have relatively low neural survival. As such, the stimulation current 460 may be deliberately steered through areas of the cochlea 140 that have low neural survival to further reduce the chance of sound perception at the return contacts (i.e., reduce the chance for the occurrence of pitch confusion).

Figure 5:
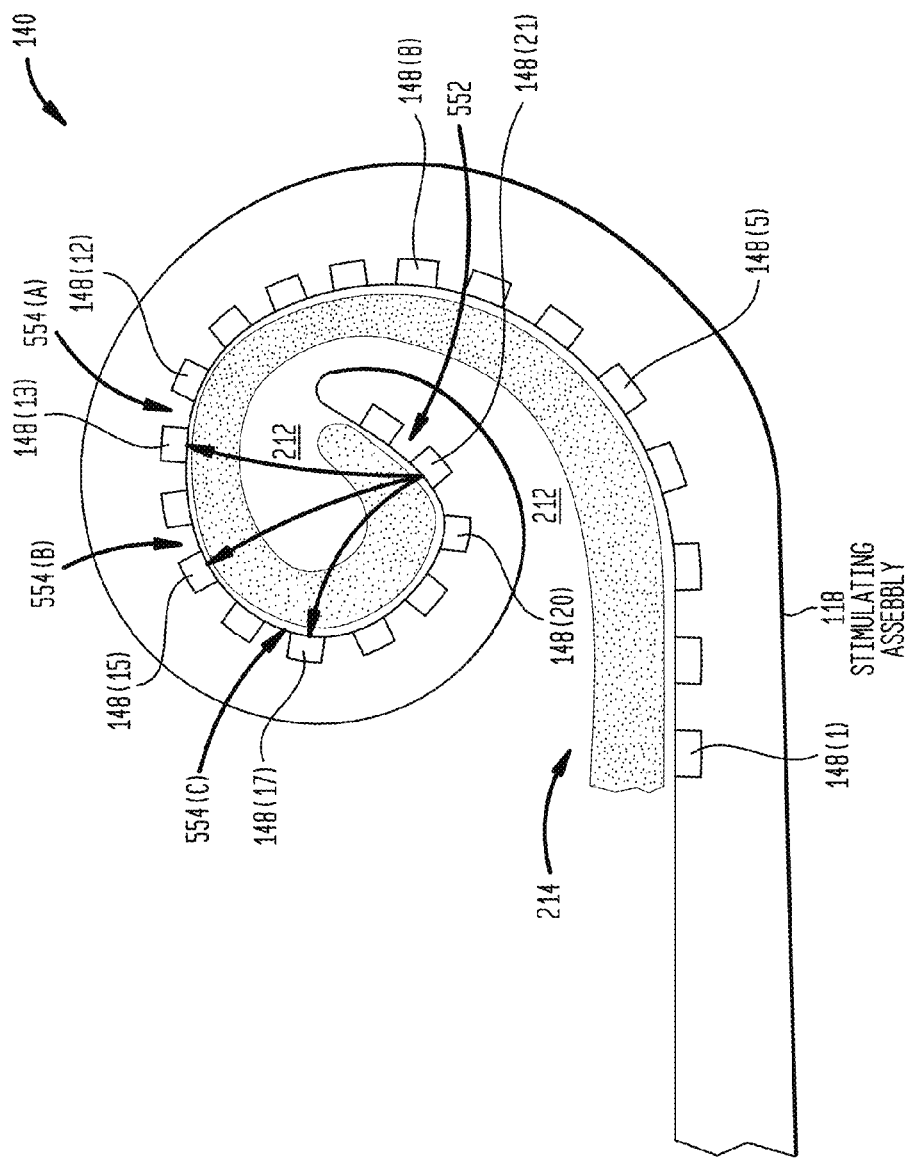
FIG. 5 is a schematic diagram illustrating the delivery of trans-modiolar stimulation to a recipient's cochlea in accordance with embodiments presented herein.
Figure 6:
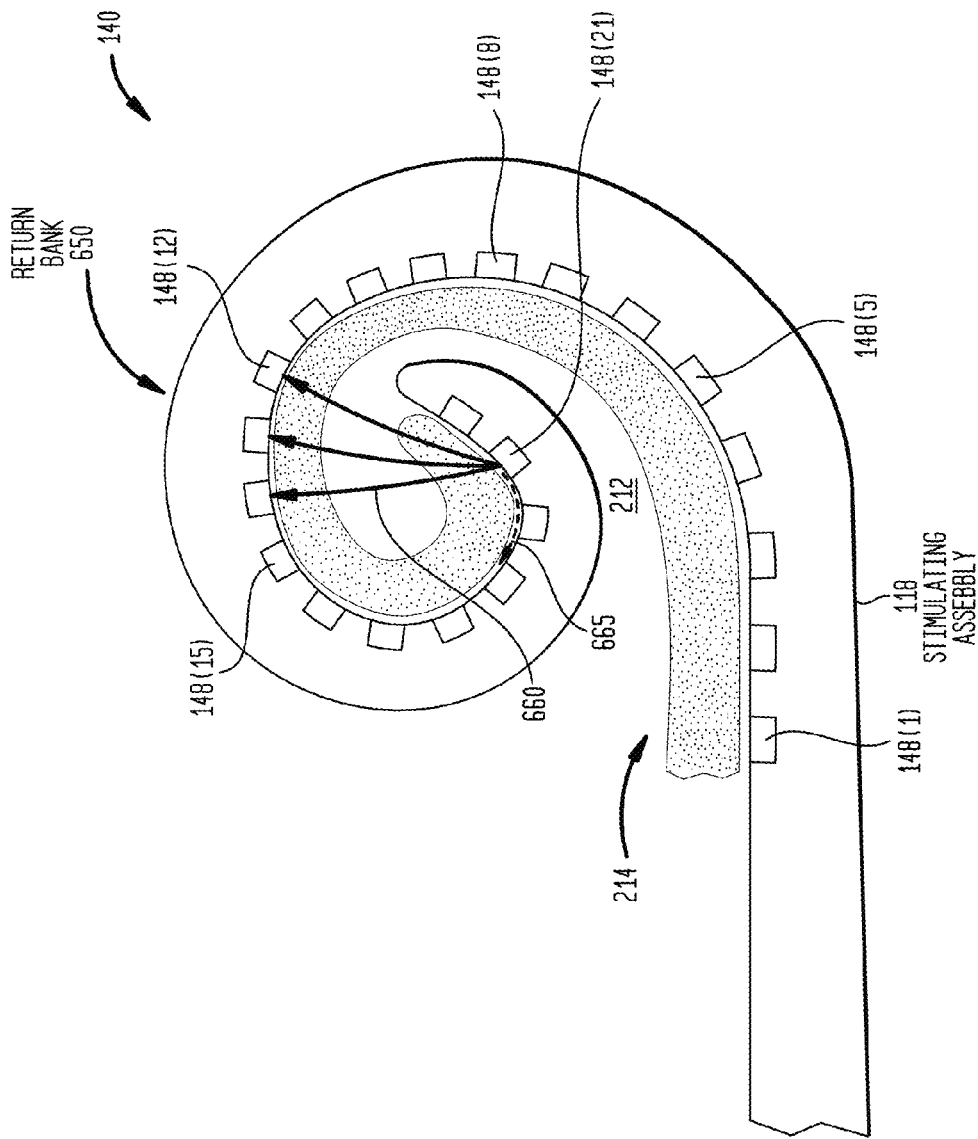
FIG. 6 is a schematic diagram illustrating the delivery of trans-modiolar stimulation to a recipient's cochlea in accordance with embodiments presented herein.

FIG. 5 illustrates another embodiment in which stimulation current 560 is delivered/sourced via stimulating contact 148(21) and sunk at a return bank 550 that includes non-adjacent return contacts (i.e., return contacts have one or more contacts that do not sink current there between). More specifically, in this example the return bank 550 includes stimulating contacts 148(13), 148(15), and 148(17), but does not include stimulating contacts 148(14) and 148(16). In other words, the return bank 550 omits stimulating contacts 148(14) and 148(16) such that all of the return contacts are non-adjacent to one another.

A portion of the stimulation current 560 passes through the modiolus 212. More specifically, in FIG. 5 the stimulation current 560 enters the modiolus 212 at a first discrete population 552 of spiral ganglion cells 214 that is adjacent to target contact 148(21). A first portion of the stimulation current 560 exits the modiolus 212 at a second population 554(A) of spiral ganglion cells 214 that is adjacent to the return contact 148(13), a second portion of the stimulation current 560 exits the modiolus 212 at a third population 554(B) of spiral ganglion cells 214 that is adjacent to the return contacts 148(15), and a third portion of the stimulation current 560 exits the modiolus 212 at a fourth population 554(C) of spiral ganglion cells 214 that is adjacent to the return contacts 148(16). As shown, the second, third, and fourth populations of spiral ganglion cells 214 are each physically separated from the first population 552 of spiral ganglion cells 214.

In addition to the neural survival issues described above, it is also known that the perilymph of the scala tympani is highly conductive (more so than the bone and the nerve). As such, it is inherent that at least some stimulation current flows through the perilymph without entering the target population of spiral ganglion cells. In such embodiments, the return bank could be located/configured so as to counteract or oppose this tendency. For example, in the context of FIG. 6, there is tendency for the stimulation current to flow from the target contact 148(21) in a generally clockwise direction through the perilymph (i.e., away from the cochlea apex) as shown by arrow 661. As such, a return bank 650 is selected so as to steer the current in the opposite direction (i.e., bias against the tendency to spread through the perilymph). In essence, the return bank 650 of FIG. 6, including return contacts 148(12), 148(13), and 148(14), pulls the stimulation current 660 counterclockwise to balance the tendency of the current to flow in the opposite direction.

Figure 7:
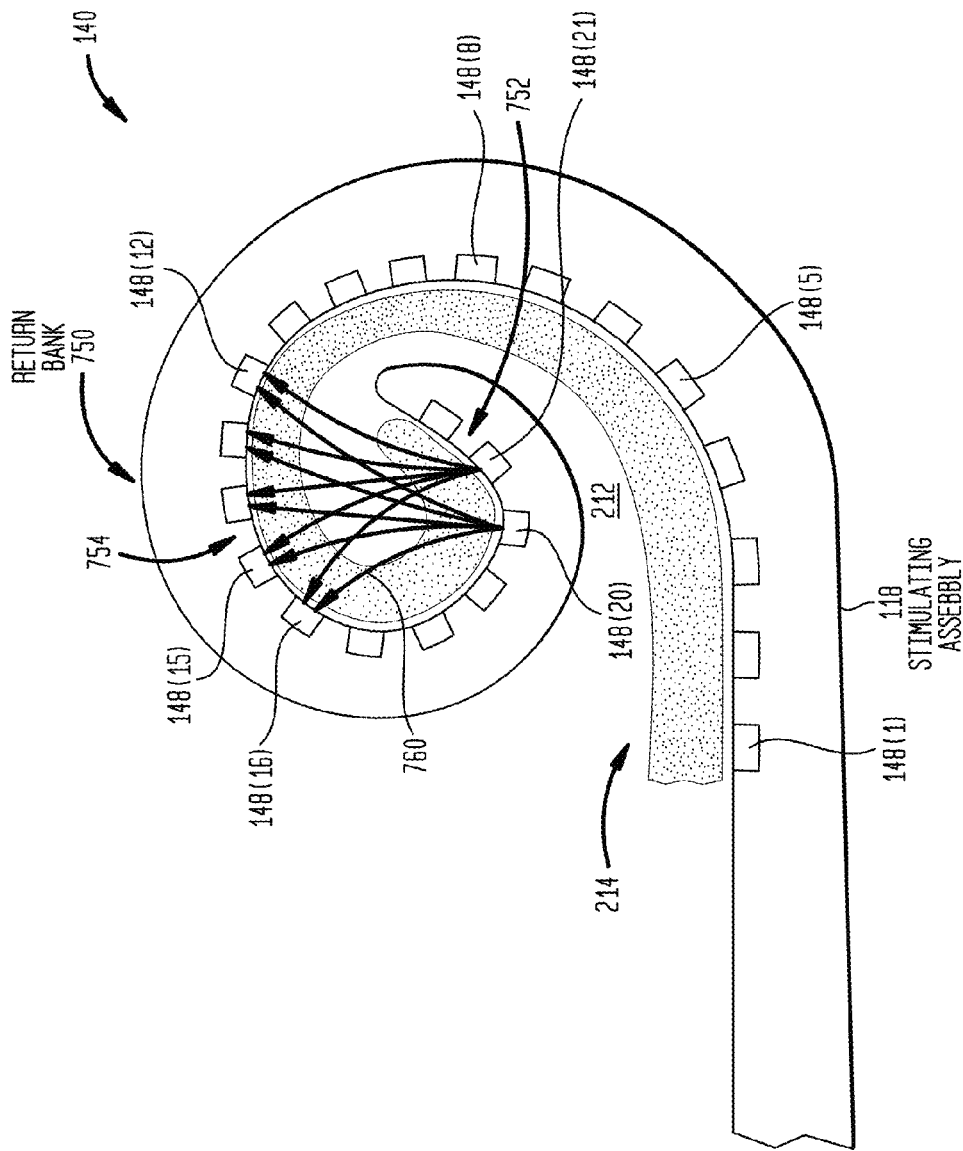
FIG. 7 is a schematic diagram illustrating the delivery of trans-modiolar stimulation to a recipient's cochlea in accordance with embodiments presented herein.

Merely for ease of illustration, the embodiments of FIGS. 3-6 have been described with reference to the use of a single target contact. FIG. 7 illustrates another embodiment of the trans-modiolar stimulation techniques in which a group (plurality) of target contacts is used to deliver stimulation current. More specifically, in the embodiment of FIG. 7, the stimulation current 760 is sourced via stimulating contacts 148(20) and 148(21). The stimulation current 760 is sunk by a return bank 750 that includes stimulating contacts 148(13) through 148(17).

Similar to the above embodiments, a substantial portion of the stimulation current 760 passes through the modiolus 212. More specifically, in FIG. 7, the stimulation current 760 enters the modiolus 212 at a first population 752 of spiral ganglion cells 214 that is adjacent to target contacts 148(20) and 148(21). A stimulation current 760 exits the modiolus 212 at a second population 754 of spiral ganglion cells 214 that is adjacent to the return contacts 148(13)-148(17). As shown, the second population 754 of spiral ganglion cells 214 is physically separated from the first population 752 of spiral ganglion cells 214.

Figure 8:
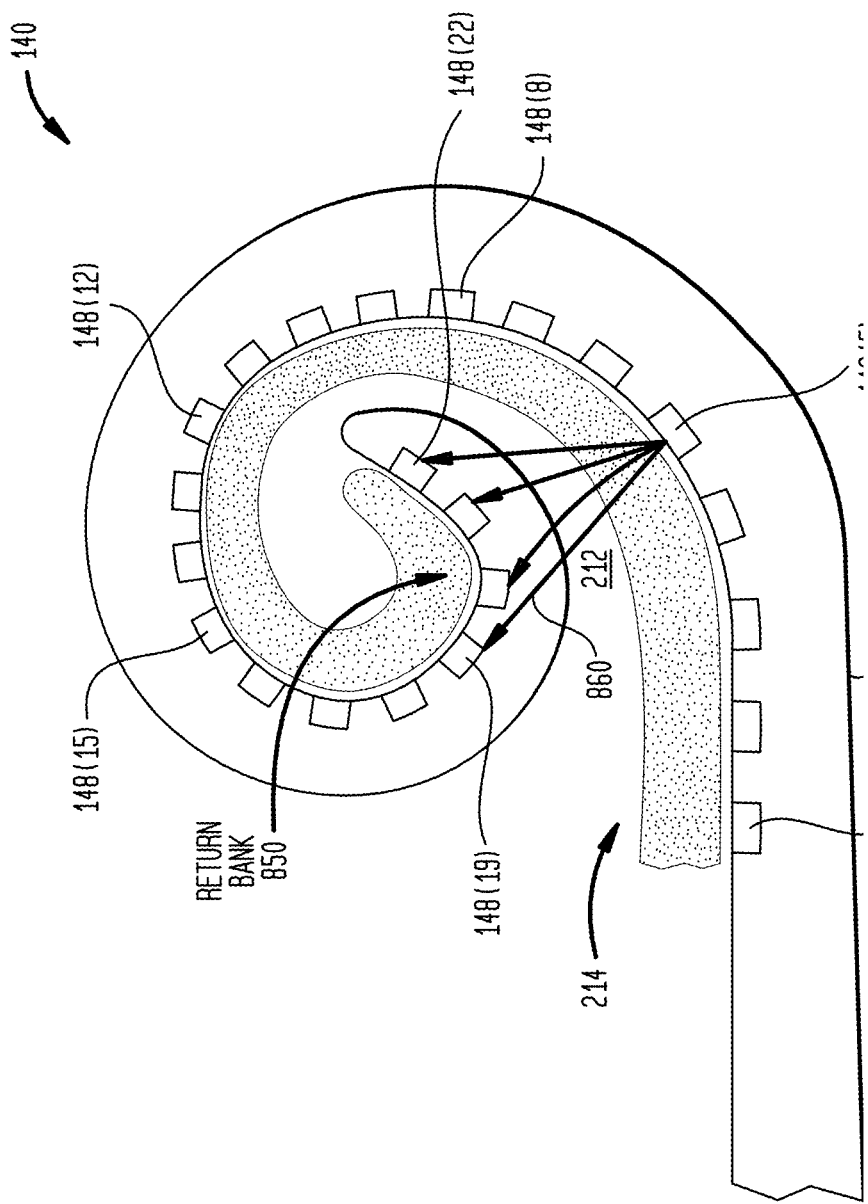
FIG. 8 is a schematic diagram illustrating the delivery of trans-modiolar stimulation to a recipient's cochlea in accordance with embodiments presented herein.

Merely for ease of illustration, the embodiments of FIGS. 3-7 have been described with reference to source and return contacts near the apical end of the cochlea 140. It is to be appreciated that the trans-modiolar stimulation techniques may be applied in other regions of the cochlea. For example, FIG. 8 illustrates an embodiment in which stimulation current 860 is delivered/sourced via stimulating contact 148(5) and is sunk at a return bank 850 that includes stimulating contacts 148(19), 148(20), 148(21), and 148(22). Similar to the above embodiments, a substantial portion of the stimulation current 860 passes through the modiolus 212.

As noted above, the trans-modiolar stimulation techniques presented herein generally used a combination of intra-cochlear contacts to sink stimulation current. In certain embodiments of the present invention, the trans-modiolar stimulation may be combined with other stimulation methods (e.g., monopolar stimulation, bipolar stimulation, tripolar stimulation, phased array stimulation, etc.). For example, FIG. 9 illustrates an embodiment in which trans-modiolar stimulation is used in combination with monopolar stimulation.

Figure 9:
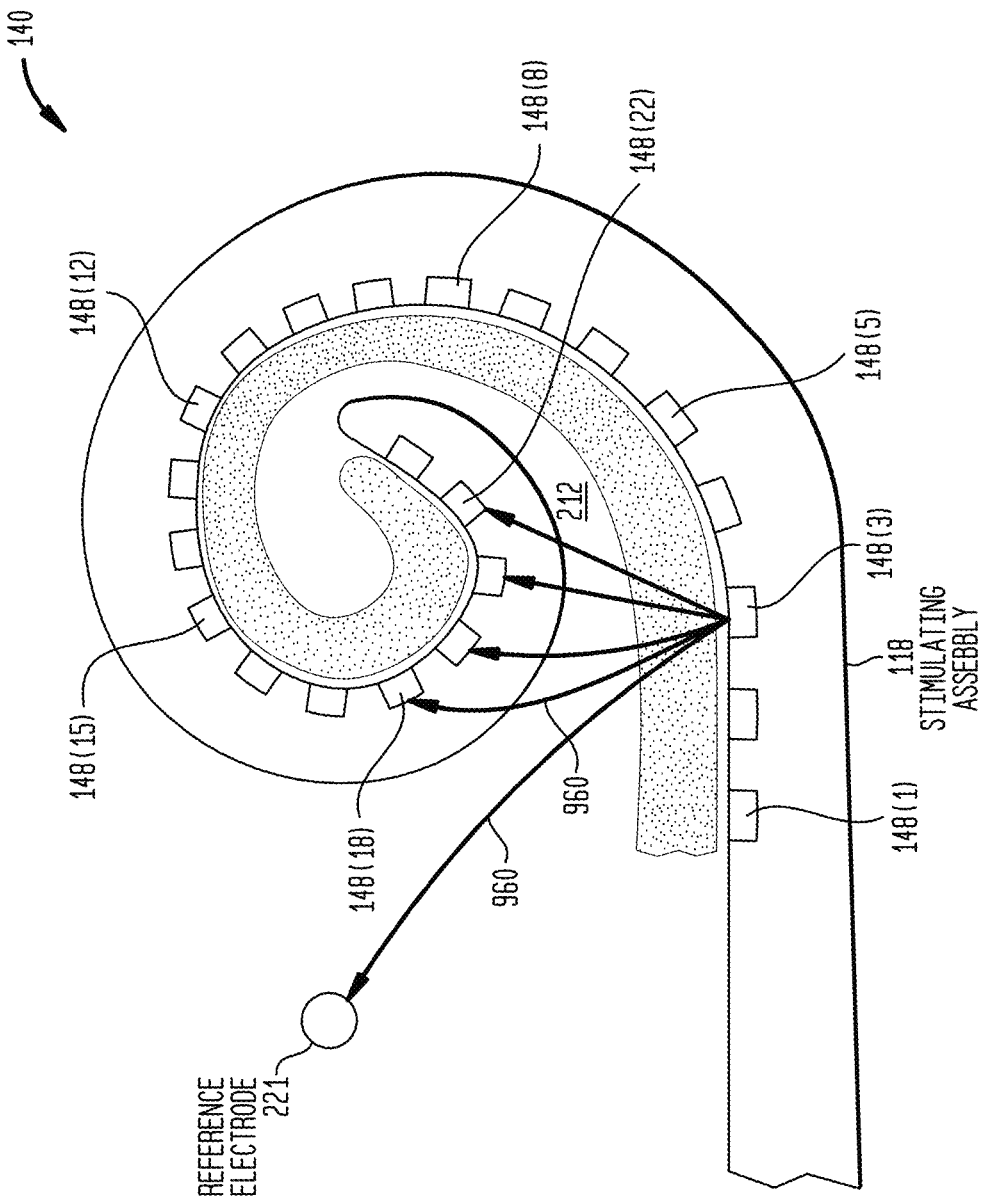
FIG. 9 is a schematic diagram illustrating the delivery of trans-modiolar stimulation in combination with monopolar stimulation to a recipient's cochlea in accordance with embodiments presented herein.

In the embodiment of FIG. 9, stimulation current 960 is sourced via stimulating contact 148(3). A first portion of the stimulation current 960 passes through modiolus 212 to a return bank 950 comprised of stimulating contacts 148(18) through 148(21). A second portion of the stimulation current flows from target contact 148(3) to reference contact 221 positioned outside of the cochlea 140. As such, the first portion of the stimulation current 960 flows in a trans-modiolar manner (i.e., through the modiolus 212), while the second portion flows in a monopolar manner (i.e., from a target contact to an extra-cochlear contact).

FIG. 9 illustrates the use of trans-modiolar stimulation in combination with monopolar stimulation at the same target contact. In alternative embodiments, trans-modiolar stimulation and monopolar stimulation may be used in combination at different contacts. In other words, stimulation current sourced via a first target contact may be sunk solely at a trans-modiolar return bank, while stimulation current sequentially or substantially simultaneously delivered via a second target contact may be sunk solely at the reference electrode 221. Embodiments that utilize the reference contact 221 may further reduce the current density adjacent to the return contacts 148(18) through 148(21) so as to avoid pitch confusion.

FIG. 10 illustrates a method 1070 in accordance with embodiments presented herein for stimulating a recipient of a cochlear implant that includes a plurality of stimulating contacts. The stimulating contacts are configured to be implanted in a recipient's cochlea such that the stimulating contacts are disposed at different locations around at least a portion of the cochlea modiolus. Method 1070 begins at 1072 wherein stimulation current is delivered via at least one stimulating contact such that the stimulation current enters the modiolus at a first population of spiral ganglion cells. At 1074, the stimulation current is sunk via a plurality of other stimulating contacts forming a return bank such that the stimulation current exits the modiolus at a second population of spiral ganglion cells that is physically separated from the first population of spiral ganglion cells.

In certain examples, the amount of current sunk at each of the plurality of other stimulating contacts in the return bank is weighted relative to one another such that at least two of the other stimulating contacts in the return bank do not sink the same amount of current. The return bank may comprise a sequence of adjacent stimulating contacts or a group of two or more non-adjacent stimulating contacts.

Figure 11:
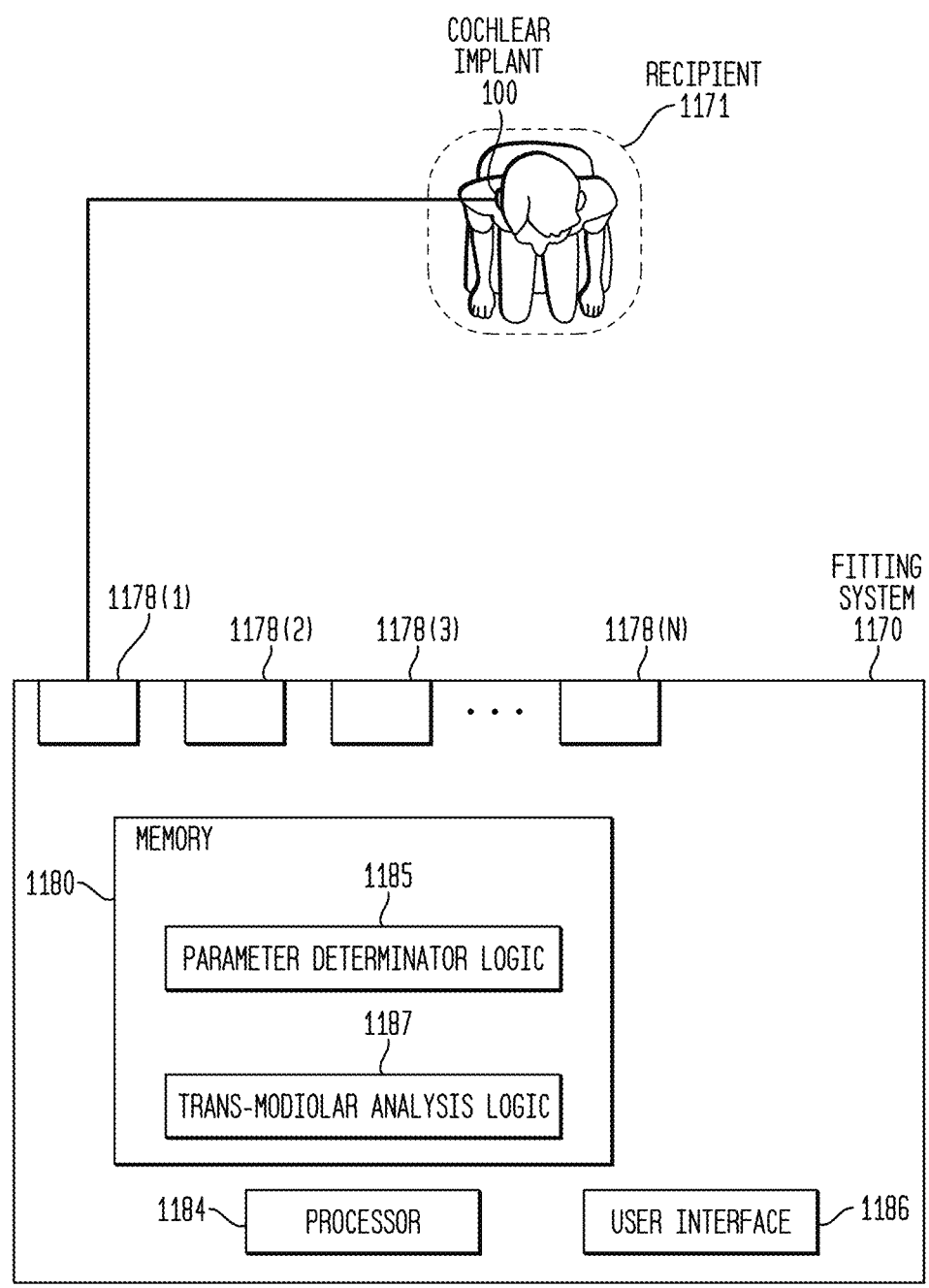
FIG. 11 is a block diagram of a fitting system in accordance with embodiments presented herein.

As noted above, a number of parameters (e.g., recipient-specific parameters, contact position/location, etc.) may affect the number and/or location of return contacts, how the current sources are weighted to sink current from the return contacts, how the current should be steered within the cochlea, etc. Embodiments of the present invention are directed to a fitting system and fitting method that can be used to obtain and/or determine various parameters and use those parameters to select/set any one or more of: (1) a target contact location, (2) a return bank location/configuration, (3) current sinking weights, etc. FIG. 11 illustrates an example fitting system 1170 configured for use with trans-modiolar stimulation.

Fitting system 1170 is, in general, a computing device that comprises a plurality of interfaces/ports 1178(1)-178(N), a memory 1180, a processor 1184, and a user interface 1186. The interfaces 1178(1)-1178(N) may comprise, for example, any combination of network ports (e.g., Ethernet ports), wireless network interfaces, Universal Serial Bus (USB) ports, Institute of Electrical and Electronics Engineers (IEEE) 1394 interfaces, PS/2 ports, etc. In the example of FIG. 11, interface 1178(1) is connected to cochlear implant 100 (FIG. 1) implanted in a recipient 1171. Interface 1178(1) may be directly connected to the cochlear implant or connected to an external device that is communication with the cochlear implant 100. Interface 1178(1) may be configured to receive the signals via a wired or wireless connection (e.g., telemetry, Bluetooth, etc.).

The memory 1180 includes parameter determination logic 1185 and trans-modiolar analysis logic 1187. In certain embodiments, the parameter determination logic 1185 may be executed to determine various parameters that affect the configuration of trans-modiolar stimulation or the use of trans-modiolar stimulation with other stimulation methods. The trans-modiolar analysis logic 1187 is configured to use the parameters obtained/determined by parameter determination logic 1185 to configure trans-modiolar stimulation for the recipient. That is, the trans-modiolar analysis logic 1187 includes a trans-modiolar analysis algorithm that may be used to select, for example, target contact location, return bank location/configuration, current sinking weights, combinations of trans-modiolar stimulation and other stimulation methods, etc. In other words, the trans-modiolar analysis logic 1187 enables the fitting system to set and optimize the use of trans-modiolar stimulation by the cochlear implant 100.

For example, in one illustrative arrangement, the parameter determination logic 1185 may be used to probe the recipient's cochlea with stimulation signals to determine, using objective and/or subjective feedback, the neural survival of different regions of the cochlea. These neural survival determinations may then be used by the trans-modiolar analysis logic 1187.

Memory 1180 may comprise read only memory (ROM), random access memory (RAM), magnetic disk storage media devices, optical storage media devices, flash memory devices, electrical, optical, or other physical/tangible memory storage devices. The processor 1184 is, for example, a microprocessor or microcontroller that executes instructions for the parameter determination logic 1185 and the trans-modiolar analysis logic 1187. Thus, in general, the memory 1180 may comprise one or more tangible (non-transitory) computer readable storage media (e.g., a memory device) encoded with software comprising computer executable instructions and when the software is executed (by the processor 1184) it is operable to perform the trans-modiolar fitting operations described herein in connection with the parameter determination logic 1185 and the trans-modiolar analysis logic 1187.

It is to be appreciated that the above embodiments are not mutually exclusive and may be combined with one another in various arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A cochlear implant, comprising:
a stimulating assembly comprising a plurality of stimulating contacts configured to be implanted in a recipient's cochlea such that the stimulating assembly spirals around at least a portion of the cochlea's modiolus; and
a stimulator unit configured to deliver stimulation current to the modiolus via at least one stimulating contact and configured to sink the stimulation current via a plurality of other stimulating contacts such that the stimulation current enters the modiolus at a first population of spiral ganglion cells and exits the modiolus at a second population of spiral ganglion cells that is physically separated from the first population of spiral ganglion cells,
wherein the stimulator unit is configured to deliver stimulation current to the cochlea via a plurality of stimulating contacts.

2. The cochlear implant of claim 1, wherein the stimulation current, as it exits the modiolus at the second population of nerve cells, has a level that is below a firing threshold of the second population of spiral ganglion cells.

3. The cochlear implant of claim 1, wherein the stimulator unit is configured to weight the amount of current sunk at each of the plurality of other stimulating contacts.

4. The cochlear implant of claim 1, wherein the plurality of other stimulating contacts comprises a sequence of adjacent stimulating contacts.

5. The cochlear implant of claim 1, wherein the plurality of other stimulating contacts comprises one or more non-adjacent stimulating contacts.

6. The cochlear implant of claim 1, wherein the plurality of other stimulating contacts is centered at a location that is substantially diametrically opposite the stimulating contact.

7. The cochlear implant of claim 1, further comprising:
an extracochlear electrode configured to sink a portion of the stimulation current delivered to the modiolus via at least one stimulating contact.

8. A cochlear implant, comprising:
a stimulating assembly configured to be implanted in a recipient's cochlea so as to spiral around at least a portion of the cochlea modiolus and comprising a plurality of stimulating contacts; and
a plurality of independently operable current sources, wherein a first current source among the plurality of current sources is configured to deliver trans-modiolar stimulation to the cochlea.

9. The cochlear implant of claim 8, wherein the first current source is configured to deliver stimulation current via a first stimulating contact and wherein one or more other current sources are configured to sink the stimulation current via a return bank that comprises a plurality of other stimulating contacts such that a substantial portion of the stimulation current passes through the modiolus.

10. The cochlear implant of claim 9, wherein the stimulator unit is configured to weight the amount of current sunk at each of the plurality of other stimulating contacts.

11. The cochlear implant of claim 9, wherein the plurality of other stimulating contacts in the return bank comprises a sequence of adjacent stimulating contacts.

12. The cochlear implant of claim 9, wherein the plurality of other stimulating contacts in the return bank comprises stimulating contacts that non-adjacent to one another.

13. The cochlear implant of claim 9, wherein the return bank has a central point that is located substantially diametrically opposite the stimulating contact.

14. The cochlear implant of claim 8, further comprising:
a extracochlear electrode configured to sink a portion of the stimulation delivered to the cochlea modiolus.

15. A method for stimulating a recipient of a cochlear implant that includes a plurality of stimulating contacts configured to be implanted in a recipient's cochlea such that the stimulating contacts are disposed around at least a portion of the cochlea modiolus, comprising:
delivering stimulation current via at least one stimulating contact such that the stimulation current enters the modiolus at a first population of spiral ganglion cells;
sinking the stimulation current via a plurality of other stimulating contacts such that the stimulation current exits the modiolus at a second population of spiral ganglion cells that is physically separated from the first population of spiral ganglion cells; and
selectively controlling the amount of current sunk at each of the plurality of other stimulating contacts.

16. The method of claim 15, wherein sinking the stimulation current via a plurality of other stimulating contacts comprises:
sinking the stimulation current via one or more non-adjacent stimulating contacts.

17. A method for stimulating a recipient of a cochlear implant that includes a plurality of stimulating contacts configured to be implanted in a recipient's cochlea such that the stimulating contacts are disposed around at least a portion of the cochlea modiolus, comprising:
delivering stimulation current via at least one stimulating contact such that the stimulation current enters the modiolus at a first population of spiral ganglion cells; and
sinking the stimulation current via a plurality of other stimulating contacts that are centered at a location that is substantially diametrically opposite the stimulating contact such that the stimulation current exits the modiolus at a second population of spiral ganglion cells that is physically separated from the first population of spiral ganglion cells.

18. A method for stimulating a recipient of a cochlear implant that includes a plurality of stimulating contacts configured to be implanted in a recipient's cochlea such that the stimulating contacts are disposed around at least a portion of the cochlea modiolus, comprising:
delivering stimulation current via at least one stimulating contact such that the stimulation current enters the modiolus at a first population of spiral ganglion cells; and
sinking the stimulation current via a sequence of adjacent other stimulating contacts such that the stimulation current exits the modiolus at a second population of spiral ganglion cells that is physically separated from the first population of spiral ganglion cells.

* * * * *